United States Patent [19]

Kamerling

[11] Patent Number: 4,603,697
[45] Date of Patent: Aug. 5, 1986

[54] SYSTEM FOR PREVENTING OR TREATING OPEN ANGLE GLAUCOMA AND PRESBYOPIA

[76] Inventor: William Kamerling, 423 W. Clements Bridge Rd., Barrington, N.J. 08007

[21] Appl. No.: 689,124

[22] Filed: Jan. 7, 1985

[51] Int. Cl.⁴ ............................................. A61N 1/36
[52] U.S. Cl. ................................. 128/421; 128/791
[58] Field of Search ............... 128/419 R, 421–422, 128/645, 646, 649, 745, 782, 791, 793; 623/4

[56] References Cited

U.S. PATENT DOCUMENTS

| | | | |
|---|---|---|---|
| 2,525,381 | 10/1950 | Toner | 128/793 |
| 3,236,240 | 2/1966 | Bradley | 128/421 |
| 3,363,242 | 1/1968 | Currey et al. | 128/782 |
| 3,540,453 | 11/1970 | Sugimori | 128/422 |
| 3,699,970 | 10/1972 | Brindley et al. | 128/419 R |
| 4,271,841 | 6/1981 | Friedman | 128/419 R |

OTHER PUBLICATIONS

"The Role of the Extraocular Muscles in Open-Angle Glaucoma", *Glaucoma*, vol. 1, No. 1 (Feb. 1979)—W. Kamerling et al.

*Primary Examiner*—William E. Kamm
*Attorney, Agent, or Firm*—Seidel, Gonda, Goldhammer & Abbott

[57] ABSTRACT

A system for preventing or treating open angle glaucoma and presbyopia by electrical stimulation of the ciliary muscle of the eye. In one embodiment, a body implantable unit develops an electrical stimulation signal and delivers that signal to the longitudinal fibers of the ciliary muscle, to widen the intertrabecular spaces and thereby facilitate outflow of aqueous fluid from the eye, and/or to the circular fibers of the ciliary muscle to accommodate widening of the lens of the eye. The signal developing portion of the implanted unit may include a receiver which cooperates with an external transmitting member or the signal developing portion may be a self-contained pulse generating unit. In a second embodiment, the entire unit is located outside the body and is mounted in a probe shaped holder.

18 Claims, 7 Drawing Figures

SYSTEM FOR PREVENTING OR TREATING OPEN ANGLE GLAUCOMA AND PRESBYOPIA

BACKGROUND OF THE INVENTION

Glaucoma is an ocular disorder wherein the intraocular pressure of the eye is elevated so as to cause damage to the optic nerve. This produces loss of visual field. Unless treated, the disease may gradually progress to complete blindness. Nature and causes of the disease are discussed generally in Cecil Textbook of Medicine, (15th Ed. 1979) at p. 2322 et seq. It has been estimated that 2–3% of all people over 40 years of age have glaucoma.

Primary open-angle glaucoma occurs predominantly in people over forty years of age and is the most common form of all glaucomas. In virtually all open-angle glaucomas, elevated intraocular pressure is caused by an increased resistance to outflow which results from changes in the trabecular meshwork, Schlemm's canal, or adjacent efferent channels. Open-angle glaucomas are usually treated medically by the administration of drops. When unsuccessful, medical treatment is followed by laser and/or surgical treatment.

The cause of open-angle glaucoma has been theorized as arising from an imbalance between the extraocular muscles and the longitudinal fibers of the ciliary muscle in W. Kamerling, et al., "The Role Of The Extraocular Muscles In Open-Angle Glaucoma", Glaucoma, Vol. 1, No. 1 (February 1979). The suggested treatment was to weaken the extraocular muscles so as to restore balance between the extraocular muscles and the ciliary muscle.

With age, there is a gradual sclerosis and weakening of the ciliary muscle. The muscle becomes atrophic and hyalinized. The ciliary muscle may be divided into three groups of fibers: longitudinal, radial and circular. Contraction of the longitudinal ciliary fibers opens the trabecular spaces through which the aqueous fluid of the eye exits. As the longitudinal fibers of the ciliary muscle weaken, the trabecular spaces remain narrow resulting in an increased resistance to aqueous outflow and, eventually, open angle glaucoma.

Presbyopia is a condition wherein the ability of the lens to focus on near objects becomes more difficult. The lens is connected by fibers, known as zonules, to the ciliary body of the eye. Contraction of the circular fibers of the ciliary muscle relaxes the zonules and permits the lens to widen, i.e., increase in size in its anterior-posterior diameter, and thus focus more clearly on near objects. As the circular fibers of the ciliary muscle weaken, there is a decrease in the ability of the lens to change shape and to focus on near objects resulting in presbyopia.

Electrical stimulation of the extraocular muscles (ocular recti) of the eye has been proposed to treat strabismus in U.S. Pat. No. 4,271,841 titled "Electro-ocular Stimulation System" issued June 9, 1981 to Harry G. Friedman incorporated herein by reference. The patent discloses a body implantable unit including an electrode implanted over or in the extraocular muscle. The electrode is coupled by a lead to a portion of the implantable unit which develops the stimulation signal. The purpose of the stimulation signal is to trigger contraction of the agonistic extraocular muscle.

It is an object of the present invention to provide repeated, controlled electrical stimulation of the ciliary muscle to increase aqueous outflow through the trabecular meshwork and reduce intraocular pressure and thereby prevent or treat open angle glaucoma.

It is a further object of the invention to provide such stimulation to allow the lens of the eye to widen and focus on near objects and thereby prevent or treat presbyopia.

BRIEF SUMMARY OF THE INVENTION

A system for the prevention or treatment of open angle glaucoma and/or presbyopia by electrical stimulation of the ciliary muscle of the eye. A unit develops an electrical stimulation signal and delivers the same to the longitudinal fibers of the ciliary muscle (to prevent or treat glaucoma) and/or the circular fibers of the ciliary muscle (to prevent or treat presbyopia). The unit may be located externally of the body wherein stimulation is delivered via an electrode in contact with the user's skin or the unit may be implanted in the body wherein stimulation is delivered via an electrode which is implanted over or inserted in the ciliary muscle. In the embodiment wherein the unit is implanted, the signal developing portion of the unit may include a receiver which cooperates with an external transmitting member or the signal developing portion may be a self-contained pulse generating unit. In the embodiment wherein the unit is located externally of the body, the unit may be mounted in a probe shaped holder.

DETAILED DESCRIPTION OF THE INVENTION

Figure 1A:
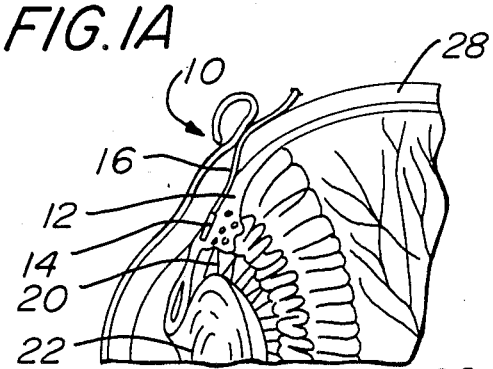
FIG. 1A is a section of the eye showing the electrode of an implantable body unit inserted in the ciliary muscle in accordance with the present invention.
Figure 1B:
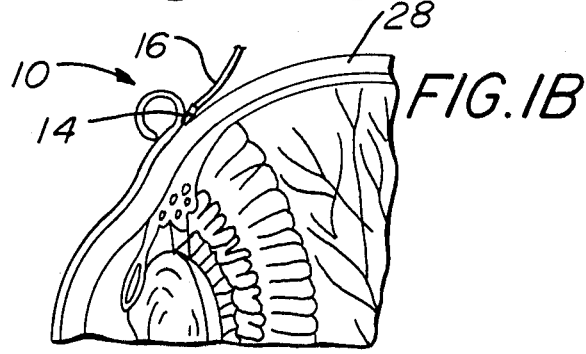
FIG. 1B is a section of the eye showing the electrode of an implantable body unit inserted over the sclera adjacent the ciliary muscle in accordance with the invention.
Figure 2:
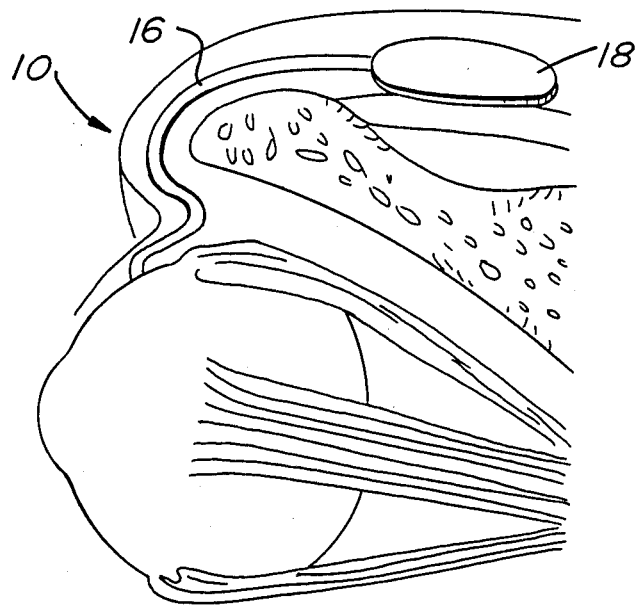
FIG. 2 illustrates the signal developing portion of the unit implanted in accordance with the present invention.

Referring to FIGS. 1A, 1B and 2, there is shown a body implantable unit 10 implanted in accordance with one embodiment of the present invention so as to provide repeated, controlled electrical stimulation to the ciliary muscle 12 of the eye. The unit 10 includes an active electrode 14 connected by a conductor or lead 16 to a signal developing portion 18 of the unit. The unit 10 is described in U.S. Pat. No. 4,369,791 titled "Body Implantable Electrode" issued Jan. 25, 1983 to Harry G. Friedman which is incorporated herein by reference.

As shown in FIG. 1, the electrode 14 is positioned so as to provide electrical stimulation to the ciliary muscle including the longitudinal and circular ciliary muscle fibers. Stimulation delivered to the ciliary muscle fibers produces contraction of the fibers. The electrode 14 is surgically inserted in (FIG. 1A) or over (FIG. 1B) the longitudinal or circular fibers of the ciliary muscle 12, so as to produce the desired contraction of the muscle fibers without interference. Contraction of the longitudinal ciliary fibers produces widening of the intertrabecular spaces so as to facilitate outflow of aqueous fluid from the eye and thereby reduce intraocular pressure to safe levels. Contraction of the circular ciliary muscle fibers causes the zonules 20 to relax so as to accommodate widening of lens 22 and thereby permit focusing on near objects.

In a preferred embodiment, the signal developing portion 18 of the implantable unit comprises a radio frequency receiver. The portion 18 of the unit generates pulse stimulation signals in response to transmitted radio frequency signals. The radio frequency signals determine the parameters of the pulse stimulation signals developed by portion 18 of the unit. Alternatively, the signal developing portion 18 may comprise a self-contained pulse generating unit. Whether the implantable unit comprises a radio frequency receiver or a self-contained pulse generating unit, it develops an electrical stimulation signal and delivers the signal to a desired stimulation site via the lead 16 and electrode 14. As disclosed in U.S. Pat. No. 4,369,791, the implantable unit may have an indifferent electrode which is carried by the housing of the unit. Other implantable units may also be adapted to the system of the present invention.

The stimulation signal developed by the unit 10 is preferably a current pulse, approximately 20 milliseconds long, which is repeated at a controlled rate. The current pulse should be repeated aperiodically, each pulse occurring randomly within a time frame of 1 to 3 seconds. The pulse may have a variable amplitude, such as 1 microamp or more, which is preselected to produce the desired therapeutic effect for the individual. The number of such pulses which are generated to provide the desired contraction of the longitudinal or circular ciliary muscle fibers will vary from individual to individual.

Figure 3:
FIG. 3 illustrates an external transmitting member which cooperates with the receiver portion of one embodiment of the implanted signal developing unit.
Figure 4:
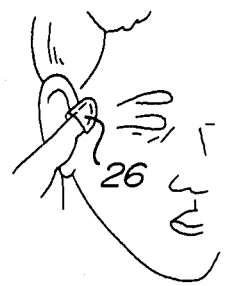
FIG. 4 illustrates the external transmitting member in a thimble type holder.

An external transmitting member or antenna 24 for cooperation with an implanted receiver is illustrated in FIG. 3. The antenna 24 is described in U.S. Pat. No. 4,271,841. The transmitter 24 is powered by a suitable miniature source and may be mounted in a thimble shaped holder 26 which mounts on the end of the user's finger as shown in FIG. 4. By bringing the holder 26 in proximity to the eye, the transmitter signals may be received by the implanted radio frequency receiver.

The electrode 14 of the unit 10 may be surgically inserted at the desired site by entering the external canthus of the eye, performing a limbal peritomy, pulling back a conjunctival tenons flap, grasping the lead or electrode and inserting the electrode and lead through the sclera 28 into the (longitudinal or circular fibers of) ciliary muscle 12 approximately 4 millimeters behind the limbus, and then closing the conjunctiva with sutures. See FIG. 1A. If desired, the end of electrode 14 may be barbed to prevent it from dislodging. Alternatively, the electrode may be grasped and positioned over the sclera 28, rather than through it, proximal the (longitudinal or circular fibers of) ciliary muscle 12. See FIG. 1B.

The signal generating portion 18 of the unit may be implanted as shown in FIG. 2 or it may be implanted in the supraclavicular area or in the back of the neck in which case lead 16 is run subcutaneously from the ear to the external canthus.

Figure 5:
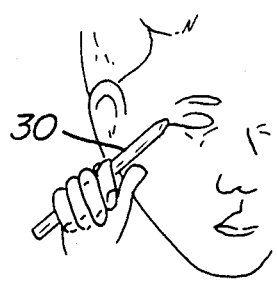
FIG. 5 illustrates a probe shaped holder for an entire unit located externally of the body.
Figure 6:
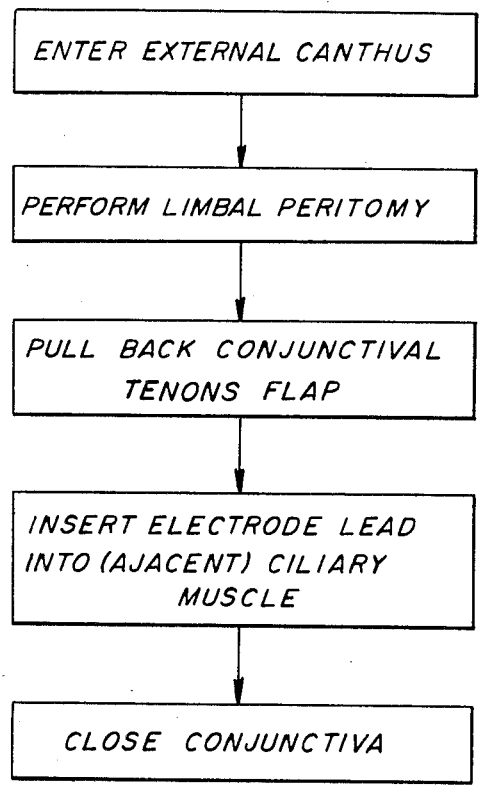
FIG. 6 is a flow chart of the steps of a surgical operation according to the present invention.

Alternatively, the entire unit may be mounted externally of the body on a probe shaped holder 30 which may be freely held by the user as shown in FIG. 5. The energy source for the unit may be stored in the user's pocket and coupled to the probe by flexible conductive wire. The probe electrode may be brought into contact with the user's skin, proximal the eye, when it is desired to stimulate the ciliary muscle fibers.

The present invention may be embodied in other specific forms without departing from the spirit or essential attributes thereof and, accordingly, reference should be made to the appended claims, rather than to the foregoing specification, as indicating the scope of the invention.

I claim:

1. Body implantable system for the prevention or treatment of open angle glaucoma by eletrical stimulation of the ciliary muscle of the eye, comprising means for developing an electrical stimulation signal, and means connected to said last-mentioned means for delivering said signal to the longitudinal fibers of the ciliary muscle.

2. Body implantable system for the prevention or treatment of presbyopia by electrical stimulation of the ciliary muscle of the eye, comprising means for developing an electrical stimulation signal, and means connected to said last-mentioned means for delivering said signal to the circular fibers of the ciliary muscle.

3. System according to claim 1 or 2 wherein said stimulation signal developing means comprises transmitting means for transmitting a high frequency signal from a location outside the body and receiving means for receiving said high frequency signal at a location inside the body and generating said electrical stimulation signal based thereon.

4. System according to claim 1 or 2 wherein said stimulation signal developing means comprise self-contained pulse generating means.

5. System according to claim 1 or 2 wherein the time occurrence of said electrical stimulation signal is aperiodic.

6. System according to claim 5 wherein said stimulation signal developing means comprises means for generating said stimulation signal in the form of a pulse occuring every one to three seconds.

7. System according to claim 6 wherein said stimulation signal developing means comprises means for generating said pulse for approximately 20 milliseconds.

8. System according to claim 7 wherein said stimulation signal developing means comprises means for adjusting the amplitude of said pulse.

9. System for inducing change in the trabecular meshwork of the eye, comprising means for developing a sequence of aperiodic electrical stimulation pulses, and means for delivering the pulses to the longitudinal fibers of the ciliary muscle of the eye.

10. System for inducing change in the shape of the lens of the eye, comprising means for developing an aperiodic sequence of electrical stimulation pulses, and means for delivering the pulses to the circular fibers of the ciliary muscle of the eye.

11. Method of preventing or treating open angle glaucoma, comprising developing a sequence of aperiodic electrical stimulation signals, and delivering said signals to the longitudinal fibers of the ciliary muscle of the eye.

12. Method of preventing or treating presbyopia, comprising developing a sequence of aperiodic electrical stimulation signals, and delivering said signals to the circular fibers of the ciliary muscle of the eye.

13. Method according to claim 11 or 12 wherein the step of developing said electrical stimulation signals includes transmitting a high frequency signal from a location outside the body and receiving said high frequency signal at a location inside the body and generating said electrical stimulation signals based thereon.

14. Method according to claim 11 or 12 wherein said step of developing said electrical stimulation signals includes developing said electrical stimulation signals every one to three seconds.

15. Method according to claim 11 or 12 wherein said electrical stimulation signal is a pulse approximately 20 milliseconds long.

16. Method according to claim 15 wherein said electrical stimulation signal has a pulse amplitude of at least one microamp.

17. Surgical method of implanting a unit including a lead connected to an electrode for electrically stimulating the ciliary muscle of the eye, comprising surgically entering the external canthus of the eye, performing a limbal peritomy, pulling back a conjunctival tenons flap, inserting the electrode through the sclera of the eye into the ciliary muscle of the eye, and closing the conjunctiva.

18. Surgical method of implanting a unit, including a lead connected to an electrode, for electrically stimulating the ciliary muscle of the eye, comprising surgically entering the external canthus of the eye, performing a limbal peritomy, pulling back a conjunctival tenons flap, placing the electrode proximal the ciliary muscle of the eye, and closing the conjunctiva.

* * * * *